(12) United States Patent
Ruebel

(10) Patent No.: US 6,852,207 B1
(45) Date of Patent: Feb. 8, 2005

(54) METHOD FOR PRODUCING PROSTHETIC MOULDED PARTS FOR DENTAL USE

(75) Inventor: Susanne Ruebel, Auerbach (DE)

(73) Assignee: Wieland Dental + Technik GmbH & Co. KG, Pforzheim (DE)

( * ) Notice: Subject to any disclaimer, the term of this patent is extended or adjusted under 35 U.S.C. 154(b) by 0 days.

(21) Appl. No.: 09/806,442

(22) PCT Filed: Sep. 30, 1999

(86) PCT No.: PCT/EP99/07257
§ 371 (c)(1),
(2), (4) Date: May 14, 2001

(87) PCT Pub. No.: WO00/19936
PCT Pub. Date: Apr. 13, 2000

(30) Foreign Application Priority Data

Oct. 2, 1998 (DE) .......................................... 198 45 506

(51) Int. Cl.[7] .............................. C25D 5/18; A61C 13/00
(52) U.S. Cl. .......................... 205/104; 205/67; 205/97; 205/266
(58) Field of Search .............................. 205/67, 96, 97, 205/103, 104, 151, 266; 204/260, 272, DIG. 7

(56) References Cited

U.S. PATENT DOCUMENTS

| | | | |
|---|---|---|---|
| 881,810 A | * 3/1908 | Lutz ........................... | 204/272 |
| 902,892 A | * 11/1908 | Lutz ........................... | 205/151 |
| 1,759,171 A | * 5/1930 | Soderberg et al. ........... | 204/242 |
| 4,192,723 A | * 3/1980 | Laude et al. ................ | 204/248 |
| 4,288,298 A | * 9/1981 | Rogers ........................ | 205/73 |
| 4,331,527 A | * 5/1982 | Metzger ...................... | 204/212 |
| 4,488,940 A | 12/1984 | Wismann | |
| 4,666,567 A | * 5/1987 | Loch ........................... | 205/83 |
| 4,820,387 A | 4/1989 | Yamashita et al. | |
| 5,316,650 A | 5/1994 | Ratzker et al. | |
| 6,071,398 A | * 6/2000 | Martin et al. ............... | 205/103 |

FOREIGN PATENT DOCUMENTS

| | | |
|---|---|---|
| DE | 728 497 | 11/1942 |
| DE | 880 783 | 6/1953 |
| DE | 32 10 315 | 9/1983 |
| DE | 89 11 651.8 | 1/1990 |
| DE | 39 19 792 | 12/1990 |
| WO | WO 92/07977 | 5/1992 |

OTHER PUBLICATIONS

George W. Jernstedt, Better Deposits At Greater Speeds By P R Plating, Plating, Jul., 1948.*

* cited by examiner

*Primary Examiner*—Roy King
*Assistant Examiner*—William T. Leader
(74) *Attorney, Agent, or Firm*—Nath & Associates PLLC; Jerald L. Meyer; Jarrod N. Raphael

(57) ABSTRACT

In a method for manufacture of prosthetic moulded parts for the dental sector with the aid of galvanic metal deposition, deposition at least partly takes place by pulse current. Deposition is preferably ended in a period of less than 5 hours, particularly within 1 to 2 hours. Deposition preferably takes place in the method of a precious metal or precious metal alloy, particularly gold or a gold alloy. Aqueous gold sulphite baths are more particularly used.

11 Claims, 1 Drawing Sheet

METHOD FOR PRODUCING PROSTHETIC MOULDED PARTS FOR DENTAL USE

Figure 1:
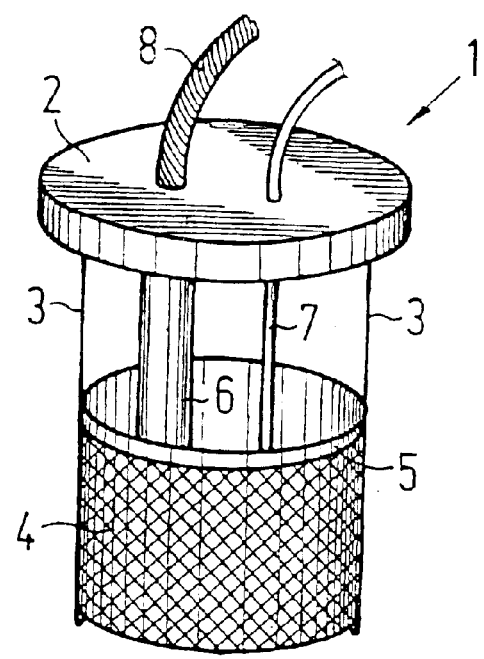

The invention mainly relates to a method for the manufacture of prosthetic moulded parts for the dental sector, particularly so-called dental frames, with the aid of galvanic metal deposition, as well as to the resulting prosthetic moulded parts.

It has long been known that an electrolytic metal deposition can also take place with pulse current, i.e. with current pulses interrupted by pauses or intervals. Such a metal deposition is also referred to as pulse-plating.

As prior art reference is e.g. made to the "pulse-plating" volume in the electroplating and surface treatment pamphlet series, Leuze-Verlag, Saulgau, 1990.

Electrolytic metal deposition with pulse current is mainly used for the application of thin metal coatings, e.g. in the electrical engineering and electronics fields. It is known that compared with deposition with direct current, pulse-plating generally is unable to bring about any increase in the deposition rate.

It is now standard procedure-in the dental sector to manufacture prosthetic moulded parts with the aid of galvanic metal deposition. The term used is galvanoforming. Mainly precious metals such as gold are used. The resulting three-dimensional moulded parts/mouldings can be used for known dental and prosthodontic purposes, particularly as so-called dental frames, to which plastic or ceramic is then applied as a veneer. Moulded parts are also galvanically produced, which are used for double crowns and bridges. It is also possible to directly use galvanically deposited mouldings.

In the commercially usable methods and devices for galvanoforming in the dental sector comparatively long galvanizing or electroplating times are involved in order to obtain a moulding with an adequate coating thickness. This is inter alia due to the fact that high quality demands are made on the coating obtained. Thus, it is necessary to have a homogeneous coating structure and a very uniform coating thickness, so as to e.g. ensure the firing stability necessary for the application of a ceramic veneer. Minimum requirements must also be fulfilled with respect to further characteristics such as porosity, wear resistance, corrosion resistance, etc. Finally, the deposited coatings must more particularly in the dental sector satisfy special esthetic demands, e.g. with regards to the brightness or surface properties.

Therefore the electroplating times for the manufacture of conventional prosthetic mouldings in dentistry when using conventional galvanizing or electroplating baths are several hours. For example the electroplating times in the case of a gold sulphite bath of the present applicant used in a versatile manner are 5 to 12 hours for the manufacture of conventional mouldings such as inlays, onlays, crowns, bridges, etc.

It is also obvious that in the dental sector use is made of all the presently known, commercially employable methods and devices for galvanoforming with d.c. plating or deposition.

The problem of the present invention is to further improve the manufacture of prosthetic dental moulded parts by galvanoforming. It is in particular to be achieved that the electroplating times can be reduced without impairing the quality of the deposited coatings. Finally, the invention is intended to provide dental prosthetics, which have at least equally good characteristics to the hitherto known dental prosthetics.

This problem is solved by a method having the features of claim 1 through 11. The wording of all the claims is hereby made by reference into part of the content of the present description.

According to the invention, the aforementioned method is characterized in that galvanic deposition takes place by pulse current deposition (pulse-plating). Pulse-plating may only represent a partial stage in the galvanic deposition overall, i.e. there is then at least one deposition stage under direct current. However, preferably galvanic metal deposition exclusively takes place by pulse-plating.

The total electroplating or deposition time in the present invention is preferably less than 5 hours, particularly less than 3 hours. In further preferred embodiments electroplating times between 1 and 2 hours are obtained.

An important parameter in the case of pulse-plating is the percentage pulse duration, i.e. the ratio of the time in which current flows to the total duration of deposition as a percentage. This quantity is also referred to as the duty cycle. In the invention percentage pulse durations between 10 and 99.9% are particularly appropriate. Within this range preference is given to values of at least 50%, preferably at least 70%. Pulse durations of at least 70% are chosen, particularly with electroplating times of less than 3 hours.

In the invention the shape of the current pulses can be freely selected. Thus, it is possible to use all known pulse current shapes, such as e.g. sinusoidal pulse currents during deposition. It is also possible to work with the aid of unipolar or bipolar (reverse pulse) pulses. Double and multiple pulses, as well as pulse overlaps are also possible. Between individual current pulses the current intensity is normally, but not necessarily reduced to zero, i.e. the current is switched off. In the invention preference is given to square-wave or ramp-shaped pulses, particular preference being given to sharply defined, square-wave current pulses. In the case of short electroplating times the latter make it possible to manufacture mouldings with smooth, bright surfaces.

In the invention the pulse current density is normally between 0.2 and 50 $A/dm^2$, especially between 1 and 20 $A/dm^2$ and in particularly preferred manner between 3 and 8 $A/dm^2$.

The duration of the current pulses ("on period") and the duration of the current pauses or intervals ("off period" in the case of an interval current 0 or time with reduced current density) can be varied in the present invention. Normally the duration of the current pulses and/or the duration of the current intervals are in the microsecond or preferably millisecond range. In general terms the duration of the current pulses and the duration of the current intervals can be the same, so that during identical time periods alternately current flows or no or a reduced current flows. It is fundamentally also possible to vary the duration of the current pulses and/or the current intervals during the electroplating time, so that there is a succession of shorter or longer time periods in which current flows or no or reduced current flows, this taking place in a regular or irregular sequence.

The duration of the current pulses (on period) is preferably at least 1 ms, particularly 20 to 100 ms. The duration of the current intervals is preferably at least 1 ms, particularly at least 4 ms, particular reference being made to off periods of 1 to 20 ms, preferably 4 to 12 ms.

For reasons of completeness it is again stated that the invention relates to the galvanic deposition of metallic dental prosthetic parts. It is correspondingly obvious that the galvanoforming method (and the devices used for the same) are inter alia matched to the dimensions and sizes of such parts. Thus, such parts normally have surfaces to be coated between 10 and 400 mm². Particular reference is made within this range to values of 30 to 250 mm², particularly 50 to 200 mm². Conventional surfaces to be coated of inlays and crowns are between 100 and 200 mm². Account is taken of these dimensions when choosing the described method parameters such as percentage pulse duration, pulse shape, pulse current density and duration of the current pulse/current interval.

As has already been stated, in the method according to the invention it is possible to manufacture by galvanoforming all conventional dental prosthetics. Preferably manufacture takes place of prosthetic moulded parts with a thickness of at least 100 μm, particularly a thickness between 150 and 300 μm by pulse-plating. Such thicknesses are particularly desired in those cases where the moulding is to be subsequently veneered by firing on ceramic material. Particularly in the case of subsequent veneering with plastics coating thicknesses below 100 μm can also be adequate.

The method according to the invention is preferably performed at a temperature above room temperature. Particularly during deposition the electroplating bath is heated to temperatures above 30° C., preferably between 50 and 80° C. Within the latter range particular reference is made to temperatures between 60 and 75° C. This measure helps to ensure a particularly rapid deposition in the present invention.

The metal deposited and which is built up by galvanoforming to a three-dimensional moulding can fundamentally be any random metal which can be deposited from an electroplating bath. In the present case mainly the metals which can be deposited in dentistry are used. Particular reference is made in the series of non-ferrous metals to nickel, chromium, cobalt and molybdenum, which are used for dental materials such as NiCr-alloys, Ni-based alloys and CrCoMo-alloys. Preferably with the method according to the invention deposition takes place of a precious metal or a precious metal alloy. These can in particular be metals from the platinum group and silver. In particular, (pure) gold or a gold alloy are deposited.

Galvanic deposition in the case of the method according to the invention normally takes place from a so-called galvanizing or electroplating bath, which contains in an adequate concentration the metal or metals to be deposited. The metal or metals to be deposited are present in the form of complexes. The baths also contain conventional additives such as deposition aids, brightening agents, etc. For ease of handling and environmental protection, in the case of the invention preference is given to the use of aqueous baths.

The method according to the invention can be performed with particular advantage using an aqueous gold sulphite bath, which in particular has a basic pH-value. Said pH-value is preferably in the range 8 to 8.5. Such a gold sulphite bath is substantially non-toxic.

When using the method according to the invention such a basic, aqueous gold sulphite bath leads to mouldings with a very uniform coating thickness and limited internal stresses. It is also possible to provide very smooth, very bright surfaces. These advantages and in particular the uniform high coating thicknesses, are achieved over the entire moulding surface, e.g. also at points with undercuts or concave depressions.

Fundamentally in the method according to the invention the already known galvanic baths, particularly the known, commercially available gold sulphite baths can be used. In order to fully utilize the advantages of the inventive method, it is preferred for the galvanic deposition to take place from a bath, which contains the metal or metals to be deposited in a higher concentration than in the hitherto known, conventional baths. For example, conventional gold sulphite baths used for depositing gold or gold alloys contain the gold in a concentration of up to 30 g/l (gram per liter). It is correspondingly preferred in the method according to the invention if the gold sulphite bath used has a gold concentration of more than 30 g/l. Gold concentrations between 40 and 60 g/l are more particularly preferred. Such baths with higher concentrations can be easily prepared by the expert on the basis of corresponding calculations and it is also possible to consider modified concentrations of further bath constituents such as brightening agents and the like.

In the invention the application of the pulse current can take place in any random, known manner. Therefore the invention covers all forms of pulsed, potentiostatic depositions, in which it is not the current, but the voltage which is varied with corresponding pulse and interval times. The decisive criterion is that the electrolytic metal deposition takes place in "pulsed" manner.

As stated, the invention also covers the prosthetic moulded part for the dental sector (dental prosthetic) obtainable by galvanoforming using the method according to the invention. This moulding is in particular manufactured according to the method of the invention. It can additionally be veneered with ceramic and/or plastic. With respect to the features and characteristics of the dental prosthetic according to the invention reference is made to the preceding description.

The invention also covers the use of pulse-plating for the manufacture of prosthetic moulded parts for the dental sector. Here reference is made once again to the previous description.

The advantages of the already described parts of the invention are inter alia that compared with the known galvanoforming methods, a much faster deposition and therefore manufacture of the moulding is possible. Thus, the dental technician performing deposition can consequently manufacture more dental prostheses than hitherto without the quality of the moulded parts being impaired. On the contrary it is possible to produce mouldings with a better coating structure and more uniform coating thickness than was hitherto the case. This more particularly applies to mouldings having a complex structure, i.e. those which e.g. have undercuts or (small) concave depressions. A further advantage is that the use of the pulse current method in galvanoforming offers numerous further method performance possibilities. Thus, as a function of the particular case, it is possible to select and optimize the pulse current density, pulse and interval times, current pulse shape, percentage pulse duration and other parameters. This is not possible to the same extent with d.c. deposition or electroplating. For example it is possible to adjust the structure, e.g. by choosing a more or less fine-grained structure, or the surface properties can be modified. With respect to the latter frequently extremely smooth surfaces are desired. The invention also makes it possible to make available surfaces of varying roughness. Such rough surfaces can be advantageous if the moulding is to be veneered after deposition. In the case of such a veneering normally production takes place in a pretreatment stage of surface roughnesses, e.g. by particle bombardment. As a result the veneering material or associated bonds adhere better. Such a pretreatment can be obviated in the case of the aforementioned production of mouldings with a rough surface.

Thus, new spheres of application are provided by the invention to galvanoforming in the dental sector, in which concentration had mainly been directed at optimizing the electroplating baths whilst maintaining d.c. electroplating and the comparatively long electroplating times.

The invention finally covers an electrolytic cell, which is provided for the manufacture of prosthetic moulded parts for the dental sector (dental prosthetics) with the aid of galvanoforming by pulse current. In particular, said electrolytic cell is used for performing the method according to the invention and for manufacturing the moulding according to the invention. The content of the originally filed claims is, by reference, made into part of the content of the present description.

According to the invention, besides other components necessary or appropriate for its function, the electrolytic cell contains an outer anode. The latter is constructed in such a way that it partly and preferably substantially completely surrounds one or more cathodes and namely along a circumferential line enclosing the cathode or cathodes. In other words the outer anode is constructed in such a way that the cathode or cathodes are located "within" the anode. The cathodes are parts which in electrolysis are located within the electrolytic cell in order to be coated with the metal or metals and in the present case e.g. prepared tooth stumps.

Provided that the above condition is fulfilled, the outer anode can fundamentally have any random design or configuration. Thus, the outer anodes can define random circumferential lines, e.g. stellate, rectangular, square or elliptical circumferential lines. Preference is given to an outer anode leading to a substantially circular circumferential line. Thus, in a preferred embodiment of the electrolytic cell according to the invention, a cylinder envelope-shaped, outer anode is used. The cylinder envelope-shaped, outer anode is preferably a so-called anode gauze, i.e. a cylinder envelope-shaped anode with an interrupted structure.

The outer anode, which partly or substantially completely encloses in its interior the cathode or cathodes, can be constructed in one piece like the aforementioned cylinder envelope-shaped anode. However, the outer anode can also comprise several anode parts along the circumferential line. It is therefore possible e.g. in the case of an anode resulting in a circular circumferential line to construct the same from two anode parts with a semicircular cross-section or four anode parts with a quadrantal cross-section. With such constructions having a multipart, outer anode it is possible to leave gaps between the individual anode parts and they can receive bath liquid.

The described electrolytic cell according to the invention preferably incorporates a further, inner anode, which (like the cathodes) is positioned within the circumferential line defined by the outer anode. This arrangement is preferably such that the cathodes are located in the area between the outer and inner anodes.

In principle the inner anode can have any random shape or configuration. Correspondingly it can be constructed in the same way as the outer anode, preferably also with a cylinder envelope shape. This means that the inner anode can be an anode gauze, which with a correspondingly smaller diameter is located within the circumferential line defined by the outer anode. In particularly preferred embodiments the inner anode is a solid anode rod.

With respect to the cathode or cathodes, the inner anode can in principle be arranged in random manner within the circumferential line defined by the outer anode. Thus, in the case where there is only one cathode in the electrolytic cell, said cathode and the inner anode face one another. The cathode and inner anode are preferably positioned symmetrically with respect to a centre, which is defined by the circumferential line of the outer anode. In electrolyte cell constructions where several cathodes are provided, the inner anode is preferably positioned centrally within the circumferential line defined by the outer anode. This has the advantage that the cathodes can be arranged symmetrically between the outer anode and the inner anode.

In a further development shielding elements are provided in the electrolytic cell according to the invention and are in particular constructed as tubular or annular elements. These shielding elements are positioned between the outer anode and the cathode parts and/or between the inner anode and the cathode parts. These shielding elements prevent the cathodes to be coated, particularly in the case of high concentrations of the metal to be deposited in the electrolytic bath, being positioned too close to the anodes. When using tubular or annular shielding elements a material exchange can only take place via the upper and/or lower, open end of the corresponding components.

Said shielding elements are preferably made from plastic, particularly Teflon.

These and further features of the invention can be gathered from the following description of preferred embodiments in conjunction with the subclaims and drawings. The individual features can be implemented individually or in the form of subcombinations. In the drawings show:

FIG. 1 A diagrammatic representation of an insert part with an outer and an inner anode for an electrolytic cell according to the invention.

Figure 2:
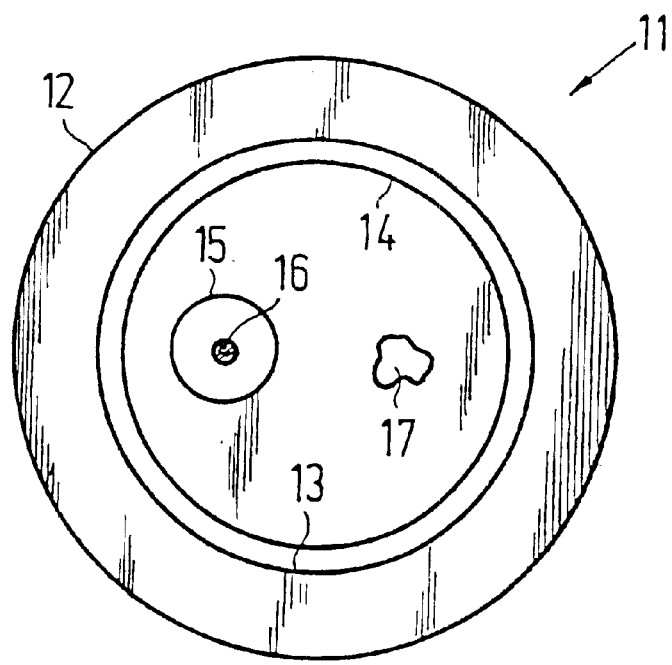

FIG. 2 A diagrammatic sectional view of an electrolytic cell according to the invention.

The insert part 1 for the electrolytic cell according to the invention and which is only diagrammatically shown in FIG. 1 has a flat upper part 2 in the manner of a lid. This upper part 2 is intended for placing or inserting the insert part 1 in an electrolytic cell. In a standard case the electrolytic cell can comprise a beaker and the insert part 1, together with further accessories.

The insert part 1 has at least two elongated holding elements 3, to which is fixed an outer anode 4 in the form of a cylinder envelope-shaped platinized titanium gauze. The holding elements 3 simultaneously serve as a feed line. The outer anode 4 defines a circular circumferential line and an inner space formed within the outer anode 4.

Directly within the outer anode 4 is provided a cylinder envelope-shaped, Teflon shielding element 5, which preferably is not in contact with the outer anode 4.

In the inner space bounded by the outer anode 4 and the shielding element 5 is located a further cylinder envelope-shaped shielding element 6, which is also made from Teflon. Said shielding element 6 is eccentrically positioned in the inner space. In the interior of the shielding element 6 is located an inner anode in the form of an anode rod and which is not shown in FIG. 1, but which is also formed from platinized titanium.

A feed line 7 for a cathode part not shown in FIG. 1 is guided through the upper part 2 of the insert part 1 facing the shielding element 6 and therefore also the inner anode. Prior to electrolysis the prepared tooth stump to be coated is e.g. fixed to said feed line 7.

Finally FIG. 1 shows a further feed line 8 for the outer anode 4 and the inner anode located within the shielding element 6. Further conventional components of an electrolytic cell are not shown in FIG. 1, but can e.g. be temperature sensors, stirrers, seals, protective rings, etc.

FIG. 2 is a diagrammatic sectional view of an electrolytic cell according to the invention. The electrolytic cell 11 has a beaker 12, which is filled with a necessary or appropriate electroplating bath quantity. In FIG. 2 it is possible to see within the beaker 12 a cylinder envelope-shaped, outer anode 13 defining a circular circumferential line. Said outer anode 13 can e.g be a platinized titanium gauze. The inner space defined by the outer anode 13 can contain, adjacent to said outer anode 13, a cylinder envelope-shaped, Teflon shielding element 14.

FIG. 2 shows another, cylinder envelope-shaped shielding element 15 eccentrically positioned in said inner space. Within said shielding element 15 is located an inner anode 16, which is in the form of a solid material rod. Symmetrically facing the shielding element 15 and inner cathode 16 is provided a tooth stump serving as the cathode part 17, which is to be coated with the aid of the electroplating bath e.g. with gold to form a dental prosthetic.

EXAMPLES

In the three following examples manufacture takes place of a dental prosthetic, which is firing-stable and to be veneered with ceramic in accordance with the galvanoforming method according to the invention. The dental prosthetic has the form of a (galvano) crown.

In all three cases a duplicate of the tooth stump is produced from the master model. This duplicating process takes place in a manner known to the expert, e.g. using plaster. Subsequently the tooth duplicate stump serving as a cathode during deposition is provided with a feed line (e.g. copper rod) and is e.g. made conductive with a conducting silver varnish.

The apparatus used for deposition is constructed essentially as shown in the drawings and comprises a heatable magnetic stirrer supplied by Heidolph (type MR 3003), a temperature sensor supplied by Heidolph (type EKT 3000) and a current/voltage source suitable for pulse-plating (potentiostat/galvanostat model 263A of EG & G). The electrolytic cell is a 100 ml beaker with a cover and a matching magnetic stirring rod. The anode comprises two anode parts, namely a cylinder envelope-shaped, platinized titanium gauze and an anode rod centrally positioned in the inner space formed by the gauze and also made from platinized titanium. For shielding the cathode part or parts, between the gauze and cathode part or parts and the rod is concentrically inserted a Teflon ring (larger diameter) or Teflon tube (smaller diameter).

An aqueous gold sulphite bath with a basic pH-value is used as the electroplating bath in all three examples. In examples 1 and 2 use is made of a gold bath with a gold concentration of 48 g/l in a 40 ml bath quantity and which is derived in known manner from a lower concentration gold bath, e.g. the bath used in example 3. In example 3 use is made of an AGC® gold bath of the present applicant with a gold concentration of 30 g/l (article no. 6781) in a bath quantity of 50 ml. In all three cases addition takes place of an AGC® brightener additive of the applicant, namely in examples 1 and 2 additive article no. 6624 (4× concentrated) in a quantity of 3 ml per cathode part and in example 3 additive article no. 6674 in a quantity of 4 ml per cathode part.

The electroplating conditions in the three examples were as follows:

EXAMPLE 1

| | |
|---|---|
| Electroplating time: | 2 hours |
| Electroplating temperature: | approx. 70° C. |
| Square-wave pulse shape: | |
| Pulse current density: | 3.6 A/dm$^2$ |
| Percentage pulse duration: | 86% |
| Current pulse duration: | 24 ms |
| Current interval duration: | 4 ms |

EXAMPLE 2

| | |
|---|---|
| Electroplating time: | 1 hour |
| Electroplating temperature: | approx. 70° C. |
| Square-wave pulse shape: | |
| Pulse current density: | 7.3 A/dm$^2$ |
| Percentage pulse duration: | 88% |
| Current pulse duration: | 24 ms |
| Current interval duration: | 4 ms |

EXAMPLE 3

| | |
|---|---|
| Electroplating time: | 4 hours |
| Electroplating temperature: | approx. 70° C. |
| Square-wave pulse shape: | |
| Pulse current density: | 1.6 A/dm$^2$ |
| Percentage pulse duration: | 88% |
| Current pulse duration: | 72 ms |
| Current interval duration: | 12 ms |

In all three examples gold-coloured, very bright galvano-crowns with an extremely smooth surface are obtained. The coating thickness of approximately 200 µm is very uniform over the entire galvano-crown and has a perfect coating structure. There is also a very uniform, fine-grained structure, which is free from voids and holes. All three galvano-crowns are firing-stable during ceramic veneering.

What is claimed is:

1. Method for the manufacture of prosthetic moulded parts for the dental sector with the aid of galvanic metal deposition, in which galvanic deposition at least partly takes place by pulse-plating, characterized in that gold or a gold alloy is deposited from a gold sulphite bath at a pulse current density of between 0.2 A/dm$^2$ and 50 A/dm$^2$ and that the percentage pulse duration, based on the total deposition time, is at least 50%.

2. Method according to claim 1, characterized in that galvanic deposition is ended in a time of less than 5 hours.

3. Method according to claim 2, characterized in that galvanic deposition is ended within 1 to 2 hours.

4. Method according to claim 1, characterized in that the percentage pulse duration is at least 70%.

5. Method according to claim 1, characterized in that square-wave or ramp-shaped current pulses are used.

6. Method according to claim 1, characterized in that the duration of the current pulses or current intervals is in the millisecond range.

7. Method according to claim 6, characterized in that the duration of the current pulses is at least 1 ms.

8. Method according to claim 6, characterized in that the duration of the current intervals is at least 1 ms.

9. Method according to claim 1, characterized in that the prosthetic moulded part is deposited with a thickness of at least 100 µm, preferably between 150 and 300 µm.

10. Method according to claim 1, characterized in that galvanic deposition takes place from an aqueous bath.

11. Method according to claim 1, characterized in that said gold sulphite bath has a gold concentration of more than 30 g/l.

* * * * *